US012611410B2

(12) United States Patent (10) Patent No.: US 12,611,410 B2
Amano et al. (45) Date of Patent: Apr. 28, 2026

(54) EMULSION, INJECTION AGENT, AND EMULSION PREPARATION METHOD

(71) Applicants: Kewpie Corporation, Tokyo (JP); FBC (Shanghai) Pharmaceutical Technology Co., Ltd., Shanghai (CN)

(72) Inventors: Yohei Amano, Chofu (JP); Kazumi Katagiri, Chofu (JP)

(73) Assignees: Kewpie Corporation, Tokyo (JP); FBC (Shanghai) Pharmaceutical Technology Co., Ltd., Shanghai (CN)

( * ) Notice: Subject to any disclaimer, the term of this patent is extended or adjusted under 35 U.S.C. 154(b) by 629 days.

(21) Appl. No.: 18/015,492

(22) PCT Filed: Apr. 15, 2021

(86) PCT No.: PCT/JP2021/015552
§ 371 (c)(1),
(2) Date: Jan. 10, 2023

(87) PCT Pub. No.: WO2022/014113
PCT Pub. Date: Jan. 20, 2022

(65) Prior Publication Data
US 2023/0310443 A1 Oct. 5, 2023

(30) Foreign Application Priority Data
Jul. 15, 2020 (JP) ................................. 2020-121438

(51) Int. Cl.
*A61K 31/5377* (2006.01)
*A61K 9/00* (2006.01)
*A61K 9/107* (2006.01)
*A61K 47/10* (2017.01)
*A61K 47/24* (2006.01)
*A61K 47/44* (2017.01)

(52) U.S. Cl.
CPC ........ *A61K 31/5377* (2013.01); *A61K 9/0019* (2013.01); *A61K 9/107* (2013.01); *A61K 47/10* (2013.01); *A61K 47/24* (2013.01); *A61K 47/44* (2013.01)

(58) Field of Classification Search
CPC .. A61K 31/5377; A61K 9/0019; A61K 9/107; A61K 47/10; A61K 47/24; A61K 47/44
USPC ....................................................... 514/230.8
See application file for complete search history.

(56) References Cited

U.S. PATENT DOCUMENTS

2018/0000829 A1 1/2018 Ottoboni et al.

FOREIGN PATENT DOCUMENTS

| CN | 102379845 A | 3/2012 |
|---|---|---|
| CN | 104619312 A | 5/2015 |
| CN | 106852118 A | 6/2017 |
| CN | 108712902 A | 10/2018 |
| CN | 110368363 A | 10/2019 |
| CN | 111388419 A | 7/2020 |
| JP | 2017-533183 A | 11/2017 |
| WO | 2016/044784 A1 | 3/2016 |

OTHER PUBLICATIONS

Shirahashi, Akihiko et al., "Side Effects and Treatment, Hypersensitivity and Infusion Reactions", Antineoplastic Drug Nippon Rinsho (Special Issue) New Cancer Pharmacotherapeutics, 72 Special Issue 2, 527-530, 529 (2014) (see partial English translation).
Suzuki, Toshiyuki, "Basics on Emulsion Technology," Colour Materials, 77(10): 462-469, 464-466 (2004) (see partial English translation).
Horiuchi, Teruo, "Basic Theories on Emulsion," J. Soc. Cosmet. Chem. Jpn. Special Summary, 44(1): 2-22 (2010) (see English abstract).
International Search Report issued in corresponding International Patent Application No. PCT/JP2021/015552 dated Jun. 1, 2021.
International Preliminary Report on Patentability and Written Opinion issued in corresponding International Patent Application No. PCT/JP2021/015552 dated Jan. 26, 2023.
Extended European Search Report issued in counterpart European Patent Application No. 21843280.5 dated Jun. 18, 2024.

*Primary Examiner* — Jeffrey H Murray
*Assistant Examiner* — Grace Ching Hsu
(74) *Attorney, Agent, or Firm* — Morgan, Lewis & Bockius LLP

(57) ABSTRACT

The present invention relates to an emulsion including aprepitant, an emulsifier, an oil, polyethylene glycol, and water, without substantial addition of ethanol.

6 Claims, No Drawings

EMULSION, INJECTION AGENT, AND EMULSION PREPARATION METHOD

TECHNICAL FIELD

The present invention relates to an emulsion, an injection agent, and an emulsion preparation method. More specifically, the present invention relates to an emulsion containing aprepitant, an injection agent, and a preparation method thereof.

BACKGROUND ART

Aprepitant is a compound having the systematic name 5-[[(2R,3S)-2-[(1R)-1-[3,5-bis(trifluoromethyl)phenyl]ethoxy]-3-(4-fluorophenyl)morpholino-4-yl]methyl]-1,2-dihydro-3H-1,2,4-triazol-3-one. Aprepitant has a neurokinin 1 (NK1) receptor antagonistic effect and is used as an anti-emetic agent to suppress nausea and vomiting which are side effects of antitumor agents.

Aprepitant is a poorly soluble compound and is mainly prepared as a preparation for oral administration. On the other hand, as a preparation suitable for parenteral administration (for example, intravenous administration), for example, Patent Literature 1 discloses an injectable emulsion containing: aprepitant; 11 weight/weight % to 15 weight/weight % of an emulsifier; an oil; a co-emulsifier which is an alcohol; a tonicity adjusting agent; a pH adjusting agent; and water, in which the pH of the emulsion is within a range of about 7.5 to 9.0.

CITATION LIST

Patent Literature

[Patent Literature 1] Japanese Unexamined Patent Publication No. 2017-533183

SUMMARY OF INVENTION

Technical Problem

According to the studies of the present inventors, there is room for improvement in stability of the emulsion disclosed in Patent Literature 1. In addition, since the emulsion disclosed in Patent Literature 1 needs to contain a high concentration of ethanol as an injection agent, it is difficult to be administered to patients who are intolerant to ethanol. Accordingly, an object of the present invention is to provide an aprepitant-containing emulsion with excellent stability without substantial addition of ethanol. Another object of the present invention is to provide an emulsion preparation method.

Solution to Problem

The present invention relates to, for example, each of the following inventions.

[1] An emulsion including: aprepitant; an emulsifier; an oil; polyethylene glycol; and water, without substantial addition of ethanol.

[2] The emulsion according to [1], further including: a pH adjusting agent, in which the pH is 8.0 to 9.0.

[3] The emulsion according to [1] or [2], in which a content of the above-described aprepitant is 0.50 w/v % to 0.90 w/v % based on a total amount of emulsion, and a content of the above-described emulsifier is 12.0 w/v % to 18.0 w/v % based on the total amount of emulsion.

[4] The emulsion according to [1] to [3], in which the above-described emulsifier is a phospholipid.

[5] The emulsion according to any one of [1] to [4], in which a content of the above-described oil is 7.0 w/v % to 12.0 w/v % based on the total amount of emulsion.

[6] The emulsion according to any one of [1] to [5], in which an average molecular weight of the above-described polyethylene glycol is 260 to 1,100.

[7] The emulsion according to any one of [1] to [6], in which a content of the above-described polyethylene glycol is 0.5 w/v % to 10.0 w/v % based on the total amount of emulsion.

[8] An injection agent including: the emulsion according to any one of [1] to [7].

[9] An emulsion preparation method including: mixing aprepitant with polyethylene glycol to produce a drug phase; mixing an emulsifier, an oil, and water with each other to produce an emulsified phase; mixing the above-described drug phase with the above-described emulsified phase to produce an emulsion; and sterilizing the above-described emulsion.

[10] The method according to claim [9], further including: incorporating a pH adjusting agent to adjust the pH of the above-described emulsion to 8.0 to 9.0.

[11] The method according to [9] or [10], in which the method does not include removing ethanol.

[12] The method according to any one of [9] to [11], in which, when producing the above-described emulsified phase, an isotonic agent and/or a buffer solution are further incorporated in addition to the above-described emulsifier, the above-described oil, and the above-described water.

Advantageous Effects of Invention

According to the present invention, it is possible to provide an aprepitant-containing emulsion with excellent stability without substantial addition of ethanol. Since the emulsion according to the present invention is substantially free of ethanol, it can be administered to patients who are intolerant to ethanol. According to the present invention, it is also possible to provide a method for preparing an aprepitant-containing emulsion with excellent stability without substantial addition of ethanol.

DESCRIPTION OF EMBODIMENT

Hereinafter, an embodiment of the present invention will be described in detail. However, the present invention is not limited to the following embodiment.

Characteristics of Present Invention (Emulsion)

The present invention is characterized by providing an emulsion containing aprepitant, an emulsifier, an oil, polyethylene glycol, and water, without substantial addition of ethanol.

(Injection Agent)

The present invention is characterized by providing an injection agent consisting of the emulsion according to the present invention.

(Emulsion Production Method)

The present invention is characterized by providing an emulsion preparation method including: mixing aprepitant with polyethylene glycol to produce a drug phase; mixing an emulsifier, an oil, and water with each other to produce an emulsified phase; mixing the drug phase with the emulsified phase to produce an emulsion; and sterilizing the emulsion.

<Emulsion>

The emulsion according to the present embodiment contains aprepitant, an emulsifier, an oil, polyethylene glycol, and water, without substantial addition of ethanol. The emulsion according to the present embodiment may be an oil-in-water type (O/W type) or a water-in-oil type (W/O type), but is preferably an oil-in-water type (O/W type) from the viewpoint that it is used as a pharmaceutical preparation.

(Aprepitant)

Aprepitant is a compound having the systematic name 5-[[(2R,3S)-2-[(1R)-1-[3,5-bis(trifluoromethyl)phenyl] ethoxy]-3-(4-fluorophenyl)morpholino-4-yl]methyl]-1,2-di-hydro-3H-1,2,4-triazol-3-one. Aprepitant may be synthe-sized by a well-known method, or a commercially available product may be obtained and used.

(Content of Aprepitant)

The content of aprepitant may be 0.50 w/v % to 0.90 w/v % based on the total amount of emulsion. The content of aprepitant within this range is pharmaceutically useful. In addition, from the viewpoint of excellent stability, the con-tent of aprepitant is preferably 0.60 w/v % to 0.80 w/v %, more preferably 0.65 w/v % to 0.75 w/v %, and still more preferably 0.70 w/v % to 0.74 w/v % based on the total amount of emulsion.

(Emulsifier)

Emulsifiers are not particularly limited as long as they are pharmaceutically acceptable. Examples of emulsifiers include glycerin fatty acid esters, sorbitan fatty acid esters, propylene glycol fatty acid esters, sucrose fatty acid esters, and phospholipids (for example, egg yolk phospholipid and soybean phospholipids). Among these, phospholipids are preferable and egg yolk phospholipids are more preferable in view of a superior effect of improving stability. The emulsifiers may be used alone or in a combination of two or more thereof. Commercially available emulsifiers may be obtained and used.

(Content of Emulsifier)

The content of an emulsifier may be 12.0 w/v % to 18.0 w/v % based on the total amount of emulsion. If the content of an emulsifier is within this range, a pharmaceutically sufficient amount of aprepitant can be solubilized. In addi-tion, from the viewpoint of excellent stability, the content of an emulsifier is, based on the total amount of emulsion, preferably 12.5 w/v % to 17.0 w/v %, more preferably 13.0 w/v % to 16.0 w/v %, still more preferably 13.5 w/v % to 15.5 w/v %, and still more preferably 14.0 w/v % to 15.0 w/v %.

(Content Ratio of Aprepitant to Emulsifier)

The content ratio of aprepitant to an emulsifier is prefer-ably 1:10 to 1:30 (weight ratio), more preferably 1:15 to 1:25 (weight ratio), and more preferably 1:18 to 1:22 (weight ratio).

(Oil)

Oils are not particularly limited as long as they are pharmaceutically acceptable. Specific examples of oils include soybean oil, olive oil, sesame oil, rapeseed oil, peanut oil, sunflower oil, corn oil, safflower oil, cottonseed oil, and medium-chain fatty acid triglycerides (MCT). Among these, soybean oil is preferable in view of a superior effect of improving stability. The oils may be used alone or in a combination of two or more thereof. Commercially available oils may be obtained and used.

(Content of Oil)

The content of an oil may be 7.0 w/v % to 12.0 w/v % based on the total amount of emulsion. If the content of an oil is within this range, a pharmaceutically sufficient amount of aprepitant can be solubilized. In addition, from the viewpoint of excellent stability, the content of an oil is, based on the total amount of emulsion, preferably 7.5 w/v % to 11.5 w/v %, more preferably 8.0 w/v % to 11.0 w/v %, still more preferably 8.5 w/v % to 10.5 w/v %, and still more preferably 9.0 w/v % to 10.0 w/v %.

(Polyethylene Glycol)

The emulsion according to the present embodiment con-tains polyethylene glycol as a solvent. Accordingly, a phar-maceutically sufficient amount of aprepitant can be solubi-lized and the stability of the emulsion can be improved.

(Average Molecular Weight of Polyethylene Glycol)

The average molecular weight of the polyethylene glycol is preferably 260 to 1,100. Accordingly, the effect of improv-ing the stability of the emulsion is more significantly exhib-ited. In addition, from the viewpoints of the effect of improving the stability of the emulsion being more signifi-cantly exhibited and higher suitability as a pharmaceutical preparation, the average molecular weight of polyethylene glycol is more preferably 260 to 800, still more preferably 260 to 600, and still more preferably 260 to 440. In the present specification, the average molecular weight of poly-ethylene glycol means a number average molecular weight.

Polyethylene glycol is not particularly limited as long as it is pharmaceutically acceptable. Polyethylene glycol may be used alone or in a combination of two or more thereof. Commercially available polyethylene glycol may be obtained and used.

Examples of commercially available polyethylene glycol include PEG 100, PEG 200, PEG 300, PEG 400, PEG 500, PEG 600, PEG 700, PEG 800, PEG 900, and PEG 1000. As polyethylene glycol, PEG300 or higher is preferable, PEG 300 to PEG 1000 are more preferable, and PEG 400 is still more preferable.

(Content of Polyethylene Glycol)

The content of polyethylene glycol may be 0.5 w/v % to 10.0 w/v % based on the total amount of emulsion. If the content of polyethylene glycol is within this range, a phar-maceutically sufficient amount of aprepitant can be solubi-lized and the stability of the emulsion can be improved. From the viewpoint of more remarkably exhibiting the effect of improving the stability of the emulsion, the content of polyethylene glycol is, based on the total amount of emul-sion, preferably 1.0 w/v % to 5.0 w/v %, more preferably 1.5 w/v % to 4.0 w/v %, still more preferably 2.0 w/v % to 3.5 w/v %, still more preferably 2.5 w/v % to 3.0 w/v %, and particularly preferably 2.8 w/v %.

(Isotonic Agent)

The emulsion according to the present embodiment may further contain an isotonic agent. An isotonic agent is added to adjust the osmotic pressure ratio of an emulsion, and is not particularly limited as long as it is pharmaceutically accept-able. As isotonic agents, it is possible to use, for example, sorbitol, xylitol, mannitol, glucose, trehalose, maltose, sucrose, raffinose, lactose, and dextran. Among these, sucrose is preferable because it has been widely used as an additive for injection agents. The isotonic agents may be used alone or in a combination of two or more thereof. Commercially available isotonic agents may be obtained and used.

(Content of Isotonic Agent)

The content of an isotonic agent may be an amount obtained by adjusting the osmotic pressure ratio of an emulsion to a desired value, or may be appropriately set. Although not limited to these, examples of the content of an isotonic agent based on the total amount of emulsion may be 0 w/v % to 25 w/v %, 0 w/v % to 20 w/v %, 0 to 15 w/v %, or 0 w/v % to 10 w/v %.

(pH Adjusting Agent)

The emulsion according to the present embodiment may further contain a pH adjusting agent. A pH adjusting agent is added to adjust the pH of an emulsion, and is not particularly limited as long as it is pharmaceutically acceptable. As pH adjusting agents, it is possible to use, for example, sodium hydroxide, potassium hydroxide, sodium carbonate, hydrochloric acid, oleic acids, potassium oleate, and sodium oleate. The pH adjusting agents may be used alone or in a combination of two or more thereof. Commercially available pH adjusting agents may be obtained and used. From the viewpoint of easily adjusting the pH of an emulsion to 8.0 to 9.0, oleic acids and oleic acid salts may be used, and sodium oleate may be particularly used.

(Content of pH Adjusting Agent)

The content of a pH adjusting agent may be an amount obtained by adjusting the pH of an emulsion to a desired value, or may be appropriately set. Although not limited to these, examples of the content of the pH adjusting agent may be 0.1 w/v % to 1 w/v %, and 0.6 w/v % to 0.8 w/v %.

(Ethanol)

The emulsion according to the present embodiment is substantially free of ethanol. In conventional aprepitant preparations, ethanol is usually added to solubilize aprepitant, but the emulsion according to the present embodiment can solubilize aprepitant without substantial addition of ethanol.

(Content of Ethanol)

Since the emulsion according to the present embodiment is substantially free of ethanol, it contains substantially no ethanol. Containing substantially no ethanol means the content of ethanol is, based on the total amount of emulsion, 0.05 w/v % or less, preferably 0.04 w/v % or less, and more preferably 0.03 w/v % or less.

(Buffer Agent)

The emulsion according to the present embodiment may further contain a buffer agent. The pH of an emulsion can be kept stable by further incorporating a buffer agent. Buffer agents are not particularly limited as long as they are pharmaceutically acceptable. Examples of buffer agents include a phosphoric acid buffer agent, a boric acid buffer agent, and a tris-buffer agent. The buffer agents may be used alone or in a combination of two or more thereof. Commercially available buffer agents may be obtained and used.

(pH of Emulsion)

The pH of the emulsion according to the present embodiment is preferably 8.0 to 9.0. If the pH is within this range, precipitation of aprepitant can be sufficiently suppressed.

(Average Particle Diameter of Emulsion)

The average particle diameter of the emulsion according to the present embodiment is usually 60 nm to 140 nm. From the viewpoint that the emulsion can be suitably used as a pharmaceutical preparation, the average particle diameter of the emulsion according to the present embodiment is preferably 70 nm to 140 nm and more preferably 80 nm to 140 nm. The average particle diameter of the emulsion can be measured through a method described in examples described below.

Since the emulsion according to the present embodiment has improved stability, an increase in average particle diameter of the emulsion during storage is suppressed. The average particle diameter of the emulsion according to the present embodiment when the emulsion is stored, for example, at 40° C. for 1 week is usually 60 nm to 140 nm, preferably 70 nm to 140 nm, and more preferably 80 nm to 140 nm. In addition, the average particle diameter of the emulsion according to the present embodiment when the emulsion is stored, for example, at 40° C. for 1 week may be within a range of 90% to 110% based on the average particle diameter before the emulsion is stored.

(Use of Emulsion)

The emulsion according to the present embodiment can be used as an aprepitant preparation. The preparation form is not particularly limited, and may be, for example, an injection agent and an oral agent. The emulsion according to the present embodiment can be suitably used as an injection agent. The usage and dosage of an aprepitant preparation can be set according to the usage and dosage of existing aprepitant preparations.

<Emulsion Preparation Method>

An emulsion preparation method according to the present includes: mixing aprepitant with polyethylene glycol to produce a drug phase (drug phase formation step); mixing an emulsifier, an oil, and water with each other to produce an emulsified phase (emulsified phase formation step); mixing the drug phase with the emulsified phase to produce an emulsion (emulsion formation step); and sterilizing the emulsion (sterilization step).

The emulsion preparation method according to the present embodiment may further include incorporating a pH adjusting agent to adjust the pH of the emulsion to 8.0 to 9.0 (pH adjustment step). The pH adjustment step is preferably carried out prior to the sterilization step.

Since the emulsion according to the present embodiment can solubilize aprepitant without substantial addition of ethanol, the emulsion preparation method according to the present embodiment does not necessarily include removing ethanol (ethanol removing step).

(Drug Phase Formation Step)

The drug phase formation step includes mixing aprepitant with polyethylene glycol to produce a drug phase. By using polyethylene glycol, a drug phase in which aprepitant is solubilized can be obtained. Examples of the conditions for mixing aprepitant with polyethylene glycol include conditions for heating and stirring at 50° C. to 70° C. at 150 to 250 rpm for 10 to 30 minutes.

(Emulsified Phase Formation Step)

The emulsified phase formation step includes mixing an emulsifier, an oil, and water with each other to produce an emulsified phase. An emulsified phase is preferably an oil-in-water type (O/W type). Examples of the conditions for mixing an emulsifier, an oil, and water with each other include conditions for heating and stirring at 50° C. to 70° C. at 5,000 to 15,000 rpm for 10 to 30 minutes. In the emulsified phase formation step, an isotonic agent and/or a buffer solution may be incorporated in addition to an emulsifier, an oil, and water to produce an emulsified phase. As the buffer solution, a solution obtained by dissolving the above-described buffer agent in water can be used, for example.

(Emulsion Formation Step)

The emulsion formation step includes mixing a drug phase with an emulsified phase to form an emulsion. The formation of an emulsion can be carried out according to a usual method.

The emulsion formation step may be carried out by forming a coarse emulsion and then finely emulsifying the coarse emulsion. The coarse emulsion can be formed by gently adding dropwise a drug phase to an emulsified phase at a constant rate and then heating and stirring the mixture at 50° C. to 70° C. at 5,000 to 15,000 rpm for 10 to 30 minutes. The average particle diameter of the coarse emulsion is usually within a range of 0.1 μm to 10 μm. Subsequently, the coarse emulsion can be finely emulsified using, for example, a high-pressure emulsifier or an ultrasonic emulsifier to produce an emulsion. The fine emulsification can be carried out, for example, by passing the liquid 3 to 30 times under a temperature condition of 50° C. to 70° C. and at a pressure of 50 to 200 MPa. The average particle diameter of an emulsion obtained through the fine emulsification is usually within a range of 50 to 150 nm. Fine emulsification using a high-pressure emulsifier or an ultrasonic emulsifier enables further refinement of the coarse emulsion. Examples of high-pressure emulsifiers include chamber-type high-pressure homogenizers such as Microfluidizer (manufactured by Microfluidics), Nanomizer (manufactured by Yoshida Kikai Co., Ltd.), and Star Burst (manufactured by Sugino Machine Limited Co., Ltd.) and homogeneous valve-type high-pressure homogenizers such as a Gaulin homogenizer (manufactured by APV), a Rannie homogenizer (manufactured by Rannie), a high-pressure homogenizer (manufactured by Niro Soavi), a homogenizer (manufactured by Sanwa machinery Trading Co., Ltd.), a high pressure homogenizer (manufactured by Izumi Food Machinery Co., Ltd.), and a ultra-high pressure homogenizer (manufactured by Ika Co., Ltd.), and examples of ultrasonic emulsifiers include Sonifier 450 (manufactured by Branson) and MIDSONIC 200 (manufactured by Kaijo Corporation).

(Sterilization Step)

The sterilization step includes sterilizing an emulsion. The sterilization of an emulsion can be carried out according to a usual method. Specifically, for example, an emulsion can be passed through a membrane filter (for example, a nylon syringe filter) with a pore diameter of 0.2 to 0.22 μm for sterilization.

(pH Adjustment Step)

The pH adjustment step includes incorporating a pH adjusting agent to adjust the pH of an emulsion to 8.0 to 9.0. The pH adjustment step may be carried out as necessary, and is not an essential step. The pH adjustment step is preferably carried out prior to the sterilization step. Specifically, the pH adjustment step can be carried out, for example, by further adding a pH adjusting agent in the drug phase formation step, further adding a pH adjusting agent in the emulsified phase formation step, and further adding a pH adjusting agent in the emulsion formation step. The amount of pH adjusting agent added can be set such that the pH of an emulsion finally obtained is within a range of 8.0 to 9.0.

The emulsion obtained through the preparation method according to the present embodiment can be suitably used for pharmaceutical applications.

EXAMPLES

Hereinafter, the present invention will be described in more detail based on test examples. However, the present invention is not limited to the following examples.

Reference Example 1: Confirmation of Stability Evaluation System (Preparation of Emulsion)

An emulsion was prepared according to the composition shown in Table 1 with reference to the method described in Patent Literature 1. Specifically, first, aprepitant (manufactured by Tokyo Chemical Industry Co., Ltd.), an egg yolk phospholipid (egg yolk lecithin E-80, manufactured by Lipoid), and soybean oil (Japanese Pharmacopoeia, soybean oil, manufactured by Kaneda Co., Ltd.) were dispersed in ethanol (first-grade ethanol manufactured by Kanto Chemical Co., Inc.). Water, sucrose (special-grade sucrose manufactured by Kanto Chemical Co., Inc.), and sodium oleate (first-grade sodium oleate manufactured by Kanto Chemical Co., Inc.) were added to the obtained solution, and the mixture was vigorously shaken and stirred for 10 minutes. The obtained mixed solution was emulsified in an ultrasonic generator (Sonifier 450 manufactured by Branson) for 20 minutes. Furthermore, a pH adjusting agent (hydrochloric acid or sodium hydroxide) was added thereto to adjust the pH of the emulsified solution to 8.0, and an emulsion was obtained. The obtained emulsion was passed through a membrane filter (Millex-GS 0.22 m manufactured by Millipore) with a pore diameter of 0.2 μm for sterilization to obtain an emulsion of a test preparation 1.

TABLE 1

| Unit: w/v % | Test preparation 1 |
| --- | --- |
| Aprepitant | 0.72 |
| Egg yolk phospholipid | 14.4 |
| Soybean oil | 9.4 |
| Ethanol | 2.8 |
| Sucrose | 5.6 |
| Sodium Oleate | 0.6 |
| Water | Remainder |

(Measurement of pH)

The pH of an emulsion was measured using a pH meter (model name: F-52) manufactured by HORIBA, Ltd.

(Measurement of Average Particle Diameter)

The average particle diameter of an emulsion was measured as a Z-average particle diameter using a measurement device (Zetasizer Nano S manufactured by Malvern Instruments Ltd.) using a dynamic light scattering method. Specifically, a laser beam of 633 nm was emitted at 25° C., and the change in scattered light intensity scattered from particles over time in microsecond units was measured. The distribution of the measured scattering intensity due to the particles were calculated through a cumulant analysis method using data analysis software (Zetasizer Nano S manufactured by Malvern Instruments Ltd.) included in the device. The cumulant analysis method is an analysis method performed through applying the distribution of the measured scattered light intensity to normal distribution to calculate the Z-average particle diameter.

(Stability Evaluation)

The prepared test preparation was stored at 5° C. for 1 month or 2 months, at 25° C. for 1 month or 2 months, or at 40° C. for 1 week, and then the average particle diameter was measured. The results are shown in Table 2. According to the stability guidelines of the International Conference on Harmonisation of Technical Requirements for Registration of Pharmaceuticals for Human Use (ICH), storage conditions of 2 months at 25° C. correspond to storage conditions of one year at 5° C.

TABLE 2

| | Average particle diameter (nm) | | | | |
|---|---|---|---|---|---|
| | Storage at 5° C. | | Storage at 25° C. | | Storage at 40° C. |
| | Before storage | After one month | After two months | After one month | After two months | After one week |
| Test preparation 1 | 68 | 69 | 69 | 96 | 171 | Separated |

As shown in Table 2, no change in average particle diameter was observed up to 2 months after storage at 5° C. An increase in average particle diameter was observed in storage at 25° C. in proportion to the storage period. In storage at 40° C., the preparation was separated into an oil phase and an aqueous phase after 1 week. These results indicate that storage at 40° C. for 1 week is under the acceleration condition equal to or higher than that of storage at 25° C. for 2 weeks. Accordingly, the subsequent stability evaluation was carried out by measuring the average particle diameter of an emulsion before and after storage at 40° C. for 1 week.

Test Example 1: Evaluation of Effects of Various Solvents on Stability

Generally pharmaceutically acceptable various solvents (ethanol, polyethylene glycol (PEG 400, manufactured by Maruishi Pharmaceutical Co., Ltd., number average molecular weight of 380 to 420), propylene glycol (PG, manufactured by Maruishi Pharmaceutical Co., Ltd.), and glycerin (Gly, manufactured by Sakamoto Yakuhin Kogyo Co., Ltd.) were used to evaluate the effects of the solvents on stability. Specifically, according to the composition shown in Table 3, emulsions of test preparations 1-1 to 1-5 were obtained in the same manner as in the method described in Reference Example 1 except that aprepitant was not incorporated.

TABLE 3

| Unit: w/v % | Test preparation 1-1 | Test preparation 1-2 | Test preparation 1-3 | Test preparation 1-4 | Test preparation 1-5 |
|---|---|---|---|---|---|
| Egg yolk phospholipid | | | 14.4 | | |
| Soy bean oil | | | 9.4 | | |
| PEG 400 | 2.8 | — | — | — | — |
| Ethanol | — | 2.8 | — | — | — |
| PG | — | — | 2.8 | — | — |
| Gly | — | — | — | 2.8 | — |
| Sucrose | | | 5.6 | | |
| Sodium Oleate | | | 0.6 | | |
| Water | | | Remainder | | |

(Stability Evaluation)

The test preparations were stored at 40° C. for 1 week, and the average particle diameter thereof before and after storage was measured. In addition, in a case where the average particle diameter after storage at 40° C. for 1 week was 140 nm or less, it was determined as "○," and especially in a case where the average particle diameter is the same as the average particle diameter before storage, it was determined as "⊘."Otherwise (in a case where the average particle diameter after storage at 40° C. for 1 week was greater than 140 nm) was determined as "x." The results are shown in Table 4.

TABLE 4

| | Test preparation 1-1 | Test preparation 1-2 | Test preparation 1-3 | Test preparation 1-4 | Test preparation 1-5 |
|---|---|---|---|---|---|
| Average particle diameter (before storage) | | | 96 nm | | |
| Average particle diameter (after storage at 40° C. for one week) | 94 nm | 100 nm | 146 nm | 164 nm | 166 nm |
| Determination | ◎ | ○ | X | X | X |

As shown in Table 4, test preparations 1-5 containing no solvent are found to have stability problems. The test preparation 1-1 which contains polyethylene glycol (PEG 400) among generally pharmaceutically acceptable various solvents and is substantially free of ethanol did not show an increase in average particle diameter even after storage at 40° C. for 1 week and had a particularly excellent effect of improving the stability.

Test Example 2: Evaluation of Effect of Polyethylene Glycol on Stability

Emulsions of test preparations 2-1 to 2-4 were obtained in the same manner as in Test Example 1 according to the composition shown in Table 5 using PEG 300 (polyethylene glycol 300, manufactured by Kanto Chemical Co., Inc., number average molecular weight of 285 to 315), PEG 400 (Japanese Pharmacopoeia, Macrogol 400, manufactured by Maruishi Pharmaceutical Co., Ltd., number average molecular weight of 380 to 420), and PEG 1000 (polyethylene glycol 1000, manufactured by Kanto Chemical Co., Inc., number average molecular weight of 950 to 1050) as polyethylene glycol. The average molecular weights of the PEGs used are all number average molecular weights calculated through a titration method.

TABLE 5

| Unit: w/v % | Test preparation 2-1 | Test preparation 2-2 | Test preparation 2-3 | Test preparation 2-4 |
|---|---|---|---|---|
| Egg yolk phospholipid | | | 14.4 | |
| Soybean oil | | | 9.4 | |
| PEG 300 | 3.0 | — | — | — |
| PEG 400 | — | 1.0 | 5.0 | — |
| PEG 1000 | — | — | — | 3.0 |
| Sucrose | | | 5.6 | |
| Sodium Oleate | | | 0.6 | |
| Water | | | Remainder | |

(Stability Evaluation)

The test preparations were stored at 40° C. for 1 week, and the average particle diameter thereof before and after storage was measured. In addition, the same criteria as in Test Example 1 were used for determination. The results are shown in Table 6.

TABLE 6

| | Test preparation 2-1 | Test preparation 2-2 | Test preparation 2-3 | Test preparation 2-4 |
|---|---|---|---|---|
| Average particle diameter (before storage) | 129 nm | | | |
| Average particle diameter (after storage at 40° C. for one week) | 121 nm | 120 nm | 124 nm | 118 nm |
| Determination | ◎ | ◎ | ◎ | ◎ |

As shown in Table 6, when the average molecular weight of polyethylene glycol was 260 or more (PEG 300 or higher), no increase in average particle diameter was observed even after storage at 40° C. for 1 week, and the effect of improving stability was particularly excellent.

Example 1: Evaluation of Stability of Aprepitant Preparation

Emulsions of example preparation 1 and comparative example preparations 1 and 2 were prepared according to the composition shown in Table 7.

Preparation of Example Preparation 1

First, aprepitant (manufactured by Tokyo Chemical Industry Co., Ltd.) was mixed with polyethylene glycol (PEG 400, Japanese Pharmacopoeia, Macrogol 400, manufactured by Maruishi Pharmaceutical Co., Ltd., number average molecular weight of 380 to 420), and the mixture was dissolved through heating and stirring at 60° C. at 200 rpm for 15 minutes to obtain a drug phase. Next, egg yolk phospholipid (egg yolk lecithin PL-100M, manufactured by Kewpie Corporation), soybean oil (Japanese Pharmacopoeia, soybean oil, manufactured by Kaneda Co., Ltd.), sucrose (special-grade sucrose, manufactured by Kanto Chemical Co., Inc.), a pH adjusting agent (first-grade sodium oleate, manufactured by Kanto Chemical Co., Inc.), and water were mixed with each other and heated and stirred at 60° C. at 8,000 rpm for 5 minutes to form an emulsified phase. Next, the drug phase was added dropwise to the emulsified phase, and the mixture was heated and stirred at 60° C. at 8,000 rpm for 5 minutes to form a coarse emulsion. Thereafter, an ultrasonic emulsifier (Sonifier 450 manufactured by Branson) was used to finely emulsify the coarse emulsion for 20 minutes. Furthermore, a pH adjusting agent (hydrochloric acid or sodium hydroxide) was added thereto to adjust the pH of the emulsified solution to 8.6, and an emulsion was obtained. The obtained emulsion was passed through a 0.2 m nylon syringe filter (Millex-GS 0.22 m manufactured by Millipore) for sterilization to obtain an emulsion of an example preparation 1.

Preparation of Comparative Example Preparations 1 and 2

An emulsion of a comparative example preparation 1 was prepared through the same procedure as the test preparation 1 in Reference Example 1. An emulsion of a comparative example preparation 2 was prepared through the same procedure as the test preparation 1 in Reference Example 1 except that ethanol was not added. The pHs of the comparative example preparations 1 and 2 were respectively 8.0 and 8.4.

TABLE 7

| Unit: w/v % | Test example preparation 1 | Comparative example preparation 1 | Comparative example preparation 2 |
|---|---|---|---|
| Aprepitant | | 0.72 | |
| Egg yolk phospholipid | | 14.4 | |
| Soybean oil | | 9.4 | |
| PEG 400 | 2.8 | — | — |
| Ethanol | — | 2.8 | — |
| Sucrose | | 5.6 | |
| Sodium Oleate | | 0.6 | |
| Water | | Remainder | |

(Stability Evaluation)

A vial was filled with each preparation, capped, and stored at 40° C. for 1 week, and the average particle diameter before and after storage was measured. In addition, the same criteria as in Test Example 1 were used for determination. Furthermore, the presence or absence of precipitation of aprepitant crystals was visually determined for each preparation after storage at 40° C. for 1 week. The results are shown in Table 8.

TABLE 8

| | Example preparation 1 | Comparative example preparation 1 | Comparative example preparation 2 |
|---|---|---|---|
| Average particle diameter (before storage) | 119 nm | 118 nm | Precipitated |
| Average particle diameter (after storage at 40° C. for 1 week) | 111 nm | 146 nm | — |
| Presence or absence of precipitation of crystals | None | None | — |
| Determination | ◎ | X | X |

As shown in Table 8, the comparative example preparation 2 prepared without solvents (polyethylene glycol and ethanol) could not even form an emulsion. After storage at 40° C. for 1 week, the example preparation 1 in which polyethylene glycol was used as a solvent had excellent stability without an increase in average particle diameter, whereas the average particle diameter of the comparative example preparation 1 in which ethanol was used as a solvent was larger than 140 nm.

Example 2: Evaluation of Stability of Aprepitant Preparation

Emulsions of example preparations 2 to 5 were prepared according to the composition shown in Table 9. The emulsions of the example preparations 2 to 5 were prepared through the same procedure as the example preparation 1 in Example 1. In the example preparation 3, oleic acid (Extra Olein 99 manufactured by NOF Corporation) was used as a pH adjusting agent instead of sodium oleate (first-grade sodium oleate manufactured by Kanto Chemical Co., Inc.). The pHs of the example preparations 2 to 5 were respectively 8.9, 8.3, 8.7, and 8.8.

TABLE 9

| Unit: w/v % | Example preparation 2 | Example preparation 3 | Example preparation 4 | Example preparation 5 |
|---|---|---|---|---|
| Aprepitant | 0.55 | 0.72 | 0.80 | 0.72 |
| Egg yolk phospholipid | 13.40 | 14.40 | 16.40 | 14.40 |
| Soybean oil | 8.40 | 9.40 | 10.50 | 9.40 |
| PEG 300 | — | — | — | 3.00 |
| PEG 400 | 1.00 | 3.00 | 5.00 | — |
| Sucrose | 5.6 | 5.6 | 5.6 | — |
| Oleic acid | — | 0.6 | — | — |
| Sodium Oleate | 0.6 | — | 0.6 | 0.6 |
| water | Remainder | | | |

(Stability Evaluation)

The same evaluation as in Example 1 was performed for each preparation. The results are shown in Table 10.

TABLE 10

| | Example preparation 2 | Example preparation 3 | Example preparation 4 | Example preparation 5 |
|---|---|---|---|---|
| Average particle diameter (before storage) | 128 nm | 109 nm | 112 nm | 113 nm |
| Average particle diameter (after storage at 40° C. for 1 week) | 118 nm | 111 nm | 137 nm | 127 nm |
| Presence or absence of precipitation of crystals | None | None | None | None |
| Determination | ◎ | ◎ | ○ | ◎ |

As shown in Table 10, the aprepitant preparations according to the present invention (example preparations 2 to 5) had excellent stability without an increase in average particle diameter even after storage at 40° C. for 1 week.

The invention claimed is:

1. An emulsion comprising:
aprepitant;
an emulsifier;
an oil;
polyethylene glycol; and
water;

wherein:
the emulsifier is egg yolk phospholipid,
the oil is soybean oil,
the polyethylene glycol is PEG 300 to PEG 1000 with an average molecular weight of the polyethylene glycol of 260 g/mol to 1,100 g/mol,
the aprepitant content is 0.50 w/v % to 0.90 w/v % based on a total amount of emulsion,
the emulsifier content is 12.0 w/v % to 18.0 w/v % based on the total amount of emulsion,
the oil content is 7.0 w/v % to 12.0 w/v % based on the total amount of emulsion,
the polyethylene glycol content is 0.5 w/v % to 10.0 w/v % based on the total amount of emulsion,
an average particle diameter is 60 nm to 140 nm, and
ethanol is present at 0.05 w/v % or less based on the total amount of the emulsion.

2. The emulsion according to claim 1, further comprising:
a pH adjusting agent;
wherein pH of the emulsion is within a range of 8.0 to 9.0.

3. An injection agent comprising:
the emulsion according to claim 1.

4. A method for preparing an emulsion according to claim 1, comprising steps of:
mixing aprepitant with polyethylene glycol to produce a drug phase;
mixing an emulsifier, an oil, and water with each other to produce an emulsified phase;
mixing the drug phase with the emulsified phase to produce an emulsion; and
sterilizing the emulsion;
wherein the method does not include removing ethanol.

5. The method according to claim 4, further comprising:
a step of incorporating a pH adjusting agent to adjust the pH of the emulsion to 8.0 to 9.0,
wherein the pH adjusting agent is at least one agent selected from the group consisting of sodium hydroxide, hydrochloric acid, oleic acid and sodium oleate.

6. The method according to claim 4,
wherein, when producing the emulsified phase, at least one selected agent from the group consisting of an isotonic agent and a buffer solution is further incorporated in addition to the emulsifier, the oil, and the water.

* * * * *